United States Patent [19]

Bapatla et al.

[11] 4,120,949
[45] Oct. 17, 1978

[54] OPHTHALMIC SOLUTION

[75] Inventors: Krishna M. Bapatla, Succasunna; Katharyn M. Brychta, Morris Plains, both of N.J.

[73] Assignee: Cooper Laboratories, Inc., Parsippany, N.J.

[21] Appl. No.: 839,332

[22] Filed: Oct. 5, 1977

[51] Int. Cl.² ............... A61K 31/74; A61K 31/79
[52] U.S. Cl. ................................. 424/80; 424/78
[58] Field of Search ............................. 424/78, 80

[56] References Cited

U.S. PATENT DOCUMENTS

| 2,861,920 | 11/1958 | Dale et al. | 424/80 |
|---|---|---|---|
| 3,311,577 | 3/1967 | Rankin | 424/80 |
| 3,843,782 | 10/1974 | Krezanoski et al. | 424/78 |
| 3,856,919 | 12/1974 | Rankin | 424/80 |
| 3,868,445 | 2/1975 | Ryde et al. | 424/78 |
| 3,920,810 | 11/1975 | Rankin | 424/80 |
| 3,927,205 | 12/1975 | Ohno et al. | 424/80 |

OTHER PUBLICATIONS

The Merck Index, 8th Ed., p. 393 (1968).

*Primary Examiner*—Albert T. Meyers
*Assistant Examiner*—D. W. Robinson
*Attorney, Agent, or Firm*—John J. Kolano; Thomas R. Boland

[57] ABSTRACT

An ophthalmic solution is disclosed comprising an aqueous solution of polyvinyl alcohol, hydroxyethyl cellulose, polyvinylpyrrolidone, and, optionally, hydroxypropyl methylcellulose. The ophthalmic solution is used in treating dry eye syndrome due to insufficient tear production in humans and mammals, and as an ocular lubricant for inflamed eyes.

8 Claims, No Drawings

OPHTHALMIC SOLUTION

BACKGROUND OF THE INVENTION

This invention relates to ophthalmic compositions for soothing and lubricating the mammalian eye. More particularly, it relates to an improved ophthalmic solution which can replace the normal tears in the eye of individuals who do not secrete enough tears.

The tears secreted by the tear glands in the mammalian eye provide a fluid layer over the surface of the conjunctiva and cornea of the mammalian eye. This film serves a number of purposes. The tear film lubricates the conjunctival membranes and cornea, keeps the cornea hydrated, and supplies nutrients to the cornea. When the tear secretion decreases due to some pathological condition or aging, there may not be enough lacrimal fluid to keep the cornea moist. When there is not enough lacrimal fluid, the continuous film which normally covers the cornea may be broken and "dry spots" appear which lead to inflammation and discomfort. This condition has been treated by periodically instilling into the eye a fluid to take the place of the natural tears. These artificial tear solutions are generally aqueous solutions containing water soluble polymers to provide the proper viscosity, surface-active agents to provide wetting properties, salts and buffers to adjust the tonicity and pH of the solution. Most of the commercially available artificial tear solutions have been either excessively viscous and, therefore, difficult to use or they do not form a sufficiently long lasting film because of their low viscosity. An artificial tear composition has now been discovered which has a superior film life time without being excessively viscous.

BRIEF DESCRIPTION OF THE INVENTION

It is an object of this invention to provide an improved ophthalmic solution suitable for use as artifical tears. It is a further object to provide an artificial tear solution having a prolonged film life time. A further object is to provide an ophthalmic solution suitable for treating inflamed eyes. A further object is to provide an improved ophthalmic solution for treating dry eye syndrome.

According to this invention, an ophthalmic solution having a relatively long film life time comprises an aqueous solution of polyvinyl alcohol, hydroxyethyl cellulose, and polyvinylpyrrolidone. The surface tension of the solution should be between 30 and 65 dynes/cm, the viscosity between 1 and 1,000 centipoises, and the pH between 6.0 and 8.0. The ophthalmic solution of this invention comprises an aqueous solution containing the following ingredients in the following proportions by weight:

| Polyvinyl alcohol | 0.1 – 10.0% |
|---|---|
| Hydroxyethyl cellulose | 0.1 – 5.0% |
| Polyvinylpyrrolidone | 0.1 – 20.0% | the proportions of the individual ingredients being chosen so that the surface tension is between 30 and 65 dynes/cm and the viscosity is between 1 and 1,000 centipoises. The ophthalmic solution should also contain a buffer system to maintain the pH of the solution between 6.0 and 8.0.

Optionally, the ophthalmic solution may contain between 0.1 and 10.0% by weight of hydroxypropyl methylcellulose.

DESCRIPTION OF THE PREFERRED EMBODIMENTS

The polyvinyl alcohol used in the ophthalmic solution of this invention may be either fully hydrolyzed or partially hydrolyzed material having average molecular weight ranging from 2,000 to 125,000. It is preferred to use polyvinyl alcohol having an average molecular weight of about 125,000.

The polyvinyl alcohol used in the composition described herein is sold by the Monsanto Company under the trademark Gelvatol ®. It is to be understood, however, that the invention is not limited to the use of any specific polyvinyl alcohol, and that any equivalent polyvinyl alcohol of pharmaceutical grade can be used to achieve equivalent results.

The hydroxyethyl cellulose used in the ophthalmic solution of this invention is a hydroxyethyl ether of cellulose, produced by treating cellulose with sodium hydroxide and reacting with ethylene oxide. Each anhydroglucose unit in the cellulose molecule has three reactive hydroxyl groups. The number substituted is known as the "degree of substitution." It is preferred to use an hydroxyethyl cellulose having a degree of substitution of about 2.5.

The hydroxyethyl cellulose used in the compositions described herein is sold by the Hercules Company under the trademark Natrosol ®. It is to be understood, however, that the invention is not limited to the use of any particular hydroxyethyl cellulose and that any equivalent hydroxyethyl cellulose of pharmaceutical grade can be used to achieve similar results.

The polyvinylpyrrolidone used in the compositions of this invention is a linear polymer of 1-vinyl-2-pyrrolidinone groups having a molecular weight of 10,000 to 40,000. Such materials are sold by GAF Corporation under the trademark Plasdone ®. It is to be understood, however, that the invention is not limited to any specific polyvinylpyrrolidone, and that any equivalent polyvinylpyrrolidone of pharmaceutical grade may be used to achieve equivalent results.

The hydroxypropyl methylcellulose used in the compositions of this invention is a propylene glycol ether of methylcellulose. Suitable material is sold by the Dow Chemical Company under the trademark Methocel ®. It is to be understood, however, that the invention is not limited to any specific hydroxypropyl methylcellulose, and that any equivalent hydroxypropyl methylcellulose may be used to achieve equivalent results.

The ophthalmic solutions of this invention preferably contain a buffer salt to control the pH. Any pharmaceutically acceptable buffer system may be used. A preferred buffer system is a mixture of monobasic and dibasic sodium phosphate in the proportions to produce the desired pH. The ophthalmic solution may have a pH between 6.0 and 8.0. A preferred pH range is 7.0–7.8 and a most preferred range is 7.4–7.8.

The ophthalmic solutions of this invention are preferably isotonic with the fluids of the mammalian eye, that is, they should have the same osmotic pressure. The tonicity may be adjusted by adding sodium chloride until the total concentration of salts in the solution and its osmotic pressure matches that of the ocular fluids.

The ophthalmic solutions of this invention preferably contain a preservative to prevent bacterial growth.

Pharmacologically acceptable preservatives such as phenylmercuric nitrate, thimerosal, and benzalkonium chloride may be used in concentrations of about 0.001 to 0.02% by weight.

The ophthalmic solutions of this invention may be prepared simply by dispersing the polymers directly in water or an isotonic buffer solution. They may also be made by first preparing stock solutions of the polymers, mixing the stock solutions in the proper proportions and diluting this with water or buffer to produce the desired concentrations.

The following examples are intended to illustrate the practice of this invention without limiting its scope. All percentages are by weight.

EXAMPLE I

Stock solutions of the polymer ingredients were prepared by dissolving the predetermined quantities of the polymer in enough water to produce 1 liter of stock solution having the following concentrations:

| Polyvinylpyrrolidone (Plasdone C-15) | 6% |
|---|---|
| Polyvinyl alcohol (Gelvatol 20-60) | 6% |
| Hydroxyethyl cellulose (Natrosol 250 G) | 2% |

Stock solutions of the phosphate buffer were prepared by dissolving 6.9 grams of monobasic sodium phosphate in 1 liter of water and titrating with 1N sodium hydroxide solution until the desired pH was attained.

Stock solutions of the preservatives were prepared by dissolving 0.08 grams in 1 liter of distilled water.

An ophthalmic solution was prepared by mixing the stock solutions in the following proportions:

| Hydroxyethyl cellulose (2% solution) | 12.5 | ml |
|---|---|---|
| Polyvinylpyrrolidone (6% solution) | 12.5 | ml |
| Polyvinyl alcohol (6% solution) | 12.5 | ml |
| Phenylmercuric nitrate (8X concentrate) | 12.5 | ml |
| Isotonic Phosphate Buffer (8X concentrate) | 12.5 | ml |
| Water, sufficient to make | 100 | ml |

Viscosity of the ophthalmic solution was measured with a Hoeppler Viscometer (falling ball) or Epprecht Rheomat-15 (a cup and bob rotational viscometer).

The surface tension was measured by using a duNouy tensiometer.

The pH was measured using a glass electrode pH meter.

The ophthalmic solution had a viscosity of 5.2 centipoises and a surface tension of 42.6 dynes/cm. The pH was 7.6 ± 0.2.

EXAMPLE II

By the procedure of Example I, an ophthalmic solution was prepared having the following composition:

| Hydroxyethyl cellulose (Natrosol 250 GR) | 1.2% |
|---|---|
| Polyvinylpyrrolidone (Plasdone C-15) | 2.0% |
| Polyvinyl alcohol (Gelvatol 20-90 BP) | 2.0% |
| Thimerosal | 0.001% |
| Disodium edetate | 0.01% | in an isotonic phosphate buffer, pH 7.6 ± 0.2

| Viscosity: | 109 centipoises |
|---|---|
| Surface tension: | 44.8 dynes/cm |

EXAMPLE III

By the procedure of Example I, an ophthalmic solution was prepared having the following composition:

| Hydroxyethyl cellulose (Natrosol 250 MR) | 0.65% |
|---|---|
| Polyvinyl alcohol (Gelvatol 20-90 BP) | 0.50% |
| Polyvinylpyrrolidone (Plasdone C-15) | 1.50% |
| Benzalkonium chloride | 0.01% |
| Disodium edetate | 0.1% | in an isotonic phosphate buffer, pH 7.6 ± 0.2

| Viscosity: | 253 centipoises |
|---|---|
| Surface tension: | 33.9 dynes/cm |

EXAMPLE IV

By the procedure of Example I, an ophthalmic solution was prepared having the following composition:

| Hydroxyethyl cellulose (Natrosol 250 GR) | 1.2% |
|---|---|
| Polyvinylpyrrolidone (Plasdone C-15) | 2.0% |
| Polyvinyl alcohol (Gelvatol 20-90 BP) | 0.5% |
| Benzalkonium chloride | 0.01% |
| Disodium edetate | 0.01% | in an isotonic phosphate buffer, pH 7.6 ± 0.2

| Viscosity: | 80 centipoises |
|---|---|
| Surface tension: | 33.6 dynes/cm |

EXAMPLE V

By the procedure of Example I, an ophthalmic vehicle was prepared having the following composition:

| Hydroxyethyl cellulose (Natrosol 250 GR) | 0.5% |
|---|---|
| Hydroxypropyl methylcellulose (Methocel HG 65) | 0.4% |
| Polyvinyl alcohol (Gelvatol 20-90 BP) | 0.5% |
| Polyvinylpyrrolidone (Plasdone C-15) | 1.0% |
| Benzalkonium chloride | 0.01% |
| Disodium edetate | 0.01% | in an isotonic phosphate buffer, pH 7.6 ± 0.2

| Viscosity: | 95 centipoises |
|---|---|
| Surface tension: | 34 dynes/cm |

EXAMPLE VI

By the procedure of Example I, an ophthalmic solution was prepared having the following composition:

| Hydroxyethyl cellulose (Natrosol 250 GR) | 0.8% |
|---|---|
| Polyvinylpyrrolidone (Plasdone C-15) | 1.5% |
| Polyvinyl alcohol (Gelvatol 20-90 BP) | 0.5% |
| Hydroxypropyl methylcellulose (Methocel HG65) | 0.4% |
| Benzalkonium chloride | 0.01% |
| Disodium edetate | 0.01% | in an isotonic phosphate buffer, pH 7.6 ± 0.2

| Viscosity: | 270 centipoises |
|---|---|
| Surface tension: | 32.97 dynes/cm |

EXAMPLE VII

By the procedure of Example I, an ophthalmic solution was prepared having the following composition:

| | |
|---|---|
| Hydroxyethyl cellulose (Natrosol 250 KR) | 0.8% |
| Polyvinylpyrrolidone (Plasdone C-15) | 1.5% |
| Polyvinyl alcohol (Gelvatol 20-90 BP) | 0.5% |
| Benzalkonium chloride | 0.01% |
| Disodium edetate | 0.01% | in an isotonic phosphate buffer, pH 7.6 ± 0.2

| | |
|---|---|
| Viscosity: | 95 centipoises |
| Surface tension: | 32.6 dynes/cm |

EXAMPLE VIII

By the procedure of Example I, an ophthalmic solution was prepared having the following composition:

| | |
|---|---|
| Polyvinyl alcohol (Gelvatol 20-90 BP) | 0.5% |
| Hydroxyethyl cellulose (Natrosol 250 KR) | 0.8% |
| Polyvinylpyrrolidone (Plasdone C-15) | 1.5% |
| Benzalkonium chloride | 0.005% |
| Disodium edetate | 0.01% | in isotonic phosphate buffer, pH 7.6 ± 0.2

| | |
|---|---|
| Viscosity: | 88 centipoises |
| Surface tension: | 36.4 dynes/cm |

EXAMPLE IX

This example illustrates the tear film break-up times (BUT) measured for the ophthalmic solutions of this invention.

Four male rhesus monkeys were selected for testing. The four monkeys weights 5.9, 6.0, 7.3, and 7.7 kgs, respectively. The monkeys were maintained on a standard commercial diet, but were starved on the day of testing. Each monkey was anesthetized and maintained with Vetalar ® (ketamine hydrochloride, 100 mg/ml) by intramuscular injection into the thigh. Once anesthetized, each monkey was immobilized to facilitate their handling by securing their hands and feet, and then wrapping their body in a cloth towel. Each restrained monkey was placed in a seated position in front of a Zeiss slit lamp. The head was supported on the chin rest and the eyes were aligned for observation. The eyelids of one eye were held open for topical instillation of one 10 μl drop of normal saline containing 0.125% sodium fluorescein. The lids were manually blinked twice in order to uniformly distribute the fluorescein and then held open for a control BUT measurement. The resultant tear film was scanned with a broad beam slit in a darkened room, using a cobalt blue filter, until the first dry spot appeared. The dry spot manifested itself as a black area, (round, oval or streak-shaped) in the fluorescent yellowish-green precorneal film. A laboratory stop watch was started immediately after the last blink and was stopped as soon as a break was observed in the tear film. This procedure was alternated between the right and left eyes until three control BUT values were measured for each eye.

Immediately after the control BUT measurements were determined, the same four monkeys were employed to test one ophthalmic solution. No more than one formulation was tested on any single day. Three BUT values for each ophthalmic vehicle were measured for each eye by employing the same methodology as described for the control, normal saline solution.

The three saline control BUT values for each eye were averaged and the three tear substitute BUT values for each eye were averaged. The mean ± S.E. of the eight eyes treated with normal saline and the mean ± S.E. of the same eight eyes treated with tear substitute were determined. A one-tailed t-test was performed to determine whether the ophthalmic vehicle was more effective than the normal saline in prolonging tear film BUT.

The measured values of tear film break-up time (BUT) are listed in Table I (S.E. = standard error). In these tests, the BUT for the normal saline controls range from 8 to 12 seconds.

TABLE I

| Solution of Example | BUT ± (S.E.) (seconds) |
|---|---|
| I | 15.6 ± 2.5 |
| II | 29.2 ± 3.7 |
| III | 20.7 ± 1.4 |
| IV | 28.1 ± 3.0 |
| V | 23.8 ± 2.2 |
| VI | 30.3 ± 1.8 |
| VII | 30.5 ± 2.8 |
| VIII | 18.6 ± 1.8 |

We claim:

1. An ophthalmic solution having the following composition:

| | |
|---|---|
| Hydroxyethyl cellulose | 0.8% |
| Polyvinylpyrrolidone | 1.5% |
| Polyvinyl alcohol | 0.5% |
| Hydroxypropyl methylcellulose | 0.4% |
| Benzalkonium chloride | 0.01% |
| Disodium edetate | 0.01% | in a physiologically acceptable aqueous phosphate buffer, having a pH of 6.0 to 8.0.

2. An ophthalmic solution according to claim 1 having a pH of 7.6 ± 0.2.

3. An ophthalmic solution having the following composition:

| | |
|---|---|
| Hydroxyethyl cellulose | 0.8% |
| Polyvinylpyrrolidone | 1.5% |
| Polyvinyl alcohol | 0.5% |
| Benzalkonium chloride | 0.01% |
| Disodium edetate | 0.01% | in a physiologically acceptable aqueous phosphate buffer, having a pH of 6.0 to 8.0.

4. An ophthalmic solution according to claim 3 having a pH of 7.6 ± 0.2.

5. An ophthalmic solution having the following composition:

| | |
|---|---|
| Hydroxyethyl cellulose | 1.2% |
| Polyvinylpyrrolidone | 2.0% |
| Polyvinyl alcohol | 2.0% |
| Thimerosal | 0.001% |
| Disodium edetate | 0.1% | in a physiologically acceptable aqueous phosphate buffer, having a pH of 6.0 to 8.0.

6. An ophthalmic solution according to claim 5 having a pH of 7.6 ± 0.2.

7. An ophthalmic solution having the following composition:

| | |
|---|---|
| Hydroxyethyl cellulose | 1.2% |
| Polyvinylpyrrolidone | 2.0% |
| Polyvinyl alcohol | 0.5% |
| Benzalkonium chloride | 0.01% |
| Disodium edetate | 0.01% | in a physiologically acceptable aqueous phosphate buffer, having a pH of 6.0 to 8.0.

8. An ophthalmic solution according to claim 7 having a pH of 7.6 ± 0.2.

* * * * *

UNITED STATES PATENT AND TRADEMARK OFFICE
CERTIFICATE OF CORRECTION

PATENT NO. : 4,120,949
DATED : October 17, 1978
INVENTOR(S) : Krishna M. Bapatla and Katharyn M. Brychta It is certified that error appears in the above-identified patent and that said Letters Patent are hereby corrected as shown below:

Column 2, line 13, "composition" should read --compositions--.
Column 5, line 39, "weights" should read --weighed--. Column 6, line 64, "0.1%" should read --0.01%--.

Signed and Sealed this

Seventeenth Day of April 1979

[SEAL]

Attest:

RUTH C. MASON
Attesting Officer

DONALD W. BANNER
Commissioner of Patents and Trademarks